(12) United States Patent
Klein (10) Patent No.: US 8,512,292 B2
(45) Date of Patent: Aug. 20, 2013

(54) INFILTRATION CANNULA

(76) Inventor: Jeffrey A. Klein, San Juan Capistrano, CA (US)

( * ) Notice: Subject to any disclaimer, the term of this patent is extended or adjusted under 35 U.S.C. 154(b) by 0 days.

(21) Appl. No.: 13/176,870

(22) Filed: Jul. 6, 2011

(65) Prior Publication Data
US 2011/0282271 A1 Nov. 17, 2011

Related U.S. Application Data

(60) Continuation of application No. 12/004,778, filed on Dec. 21, 2007, now abandoned, which is a division of application No. 10/877,566, filed on Jun. 25, 2004, now abandoned, which is a continuation-in-part of application No. 10/442,370, filed on May 21, 2003, now abandoned.

(51) Int. Cl.
*A61M 5/178* (2006.01)
(52) U.S. Cl.
USPC ........................ 604/164.01; 604/506; 604/35
(58) Field of Classification Search
USPC .................... 604/164.01, 171, 184, 239, 272, 604/506, 542
See application file for complete search history.

(56) References Cited

U.S. PATENT DOCUMENTS

| | | | |
|---|---|---|---|
| 2,708,437 A | 5/1955 | Hutchins | |
| 3,082,805 A | 3/1963 | Royce | |
| 3,732,858 A | 5/1973 | Banko | |
| 3,734,099 A | 5/1973 | Bender | |
| 3,955,579 A | 5/1976 | Bridgman | |
| 3,994,297 A | 11/1976 | Kopf | |
| 4,167,944 A | 9/1979 | Banko | |
| 4,203,444 A | 5/1980 | Bonnell et al. | |
| 4,311,140 A | 1/1982 | Bridgman | |
| 4,314,560 A | 2/1982 | Helfgott et al. | |
| 4,405,322 A | 9/1983 | Jessup | |
| 4,460,360 A | 7/1984 | Finegold | |
| 4,487,600 A | 12/1984 | Brownlie et al. | |

(Continued)

FOREIGN PATENT DOCUMENTS

FR 2777462 10/1999

OTHER PUBLICATIONS

Jeffrey Alan Klein, MD; The Tumescent Technique Anesthesia and Modified Liposuction Technique Dermatologic Clinic; vol. 8, No. 3, Jul. 1990.

(Continued)

*Primary Examiner* — Laura Bouchelle
(74) *Attorney, Agent, or Firm* — Stetina Brunda Garred & Brucker (57) ABSTRACT

An infiltration cannula and method of using the infiltration cannula during an infiltration procedure are disclosed herein. The infiltration cannula has a flexible cannula and a hub. The cannula has a proximal end and a distal end. The cannula also has a plurality of apertures disposed in a pattern about the distal end. The apertures are configured to infiltrate fluid into the subcutaneous or muscle tissue of a patient. The hub is configured to be held by a person performing the infiltration procedure. The hub has a first end and an opposing second end. The first end is attached to the proximal end of the flexible cannula and the second end includes a connector configured to connect to an input source for receiving the fluid to be infiltrated into the subcutaneous tissue of the patient. The fluid flows from the connector, through the hub and into the cannula.

15 Claims, 4 Drawing Sheets

(56) References Cited

U.S. PATENT DOCUMENTS

| | | | |
|---|---|---|---|
| 4,530,356 A | 7/1985 | Helfgott et al. | |
| 4,536,180 A | 8/1985 | Johnson | |
| 4,577,629 A | 3/1986 | Martinez | |
| 4,586,921 A * | 5/1986 | Berson | 604/512 |
| 4,589,414 A | 5/1986 | Yoshida et al. | |
| 4,713,053 A | 12/1987 | Lee | |
| 4,735,605 A | 4/1988 | Swartz | |
| 4,775,365 A | 10/1988 | Swartz | |
| 4,784,649 A | 11/1988 | Imonti et al. | |
| 4,790,830 A * | 12/1988 | Hamacher | 604/274 |
| 4,815,462 A | 3/1989 | Clark | |
| 4,850,354 A | 7/1989 | McGurk-Burleson et al. | |
| 4,886,491 A | 12/1989 | Parisi et al. | |
| 4,919,129 A | 4/1990 | Weber, Jr. | |
| 4,925,450 A | 5/1990 | Imonti et al. | |
| 4,932,935 A | 6/1990 | Swartz | |
| 4,938,743 A | 7/1990 | Lee | |
| 5,052,999 A | 10/1991 | Klein | |
| 5,112,302 A | 5/1992 | Cucin | |
| 5,181,907 A | 1/1993 | Becker | |
| 5,186,714 A | 2/1993 | Boudreault et al. | |
| 5,203,769 A | 4/1993 | Clement et al. | |
| 5,236,414 A | 8/1993 | Takasu | |
| 5,242,386 A | 9/1993 | Holzer | |
| 5,244,458 A | 9/1993 | Takasu | |
| 5,286,253 A | 2/1994 | Fucci | |
| 5,295,980 A | 3/1994 | Ersek | |
| 5,314,407 A | 5/1994 | Auth | |
| 5,348,535 A | 9/1994 | Cucin | |
| 5,352,194 A | 10/1994 | Greco et al. | |
| 5,446,070 A | 8/1995 | Mantelle | |
| 5,447,493 A | 9/1995 | Blugerman et al. | |
| 5,453,088 A | 9/1995 | Boudewiin et al. | |
| 5,472,416 A * | 12/1995 | Blugerman et al. | 604/28 |
| 5,489,291 A | 2/1996 | Wiley | |
| 5,514,086 A | 5/1996 | Parisi | |
| 5,643,198 A | 7/1997 | Cucin | |
| 5,655,544 A | 8/1997 | Johnson | |
| 5,725,495 A | 3/1998 | Strukel et al. | |
| 5,795,323 A | 8/1998 | Cucin | |
| 5,800,407 A | 9/1998 | Eldor | |
| 5,807,282 A | 9/1998 | Fowler | |
| 5,817,050 A | 10/1998 | Klein | |
| 5,884,631 A | 3/1999 | Silberg | |
| 5,947,988 A | 9/1999 | Smith | |
| 5,968,008 A | 10/1999 | Grams | |
| 6,020,196 A | 2/2000 | Hu et al. | |
| 6,039,048 A | 3/2000 | Silberg | |
| 6,071,260 A | 6/2000 | Halverson | |
| 6,102,885 A | 8/2000 | Bass | |
| 6,113,569 A | 9/2000 | Becker | |
| 6,129,701 A | 10/2000 | Cimino | |
| 6,162,202 A | 12/2000 | Sicurelli et al. | |
| 6,238,355 B1 | 5/2001 | Daum | |
| 6,280,424 B1 | 8/2001 | Chang et al. | |
| 6,375,648 B1 | 4/2002 | Edelman | |
| 6,428,499 B1 | 8/2002 | Halverson | |
| 6,436,116 B1 | 8/2002 | Spitz et al. | |
| 6,524,300 B2 | 2/2003 | Meglin | |
| 6,613,026 B1 | 9/2003 | Palasis et al. | |
| 6,685,666 B1 | 2/2004 | Fontenot | |
| 6,692,473 B2 | 2/2004 | St. Cyr et al. | |
| 6,706,026 B1 | 3/2004 | Goldstein et al. | |
| 6,916,292 B2 | 7/2005 | Morawski et al. | |
| 6,969,373 B2 * | 11/2005 | Schwartz et al. | 604/170.03 |
| 7,056,315 B2 | 6/2006 | Gonon | |
| 7,465,291 B2 | 12/2008 | Massengale | |
| 2002/0123723 A1 * | 9/2002 | Sorenson et al. | 604/164.01 |
| 2004/0215143 A1 | 10/2004 | Brady et al. | |
| 2004/0236313 A1 | 11/2004 | Klein | |
| 2006/0259111 A1 | 11/2006 | Peterson | |

OTHER PUBLICATIONS

Jeffrey A. Klein, M.D.; "The Tumescent Technique for Lipo-Suction Surgery", The American Journal of Cosmetic Surgery; vol. 4, No. 4, 1987.

Jeffrey A. Klein, M.D.; "Tumescent Technique for Regional Anesthesia Permits Lidocaine Doses of 35 mg/kg for Liposuction"; J. Dermatol. Surg. Oncol 16:3; Mar. 1990.

Jeffrey A. Klein, M.D.; "Tumescent Technique for Local Anesthesia Improves Safety in Large-Volume Lipsuction"; The American Society of Plastic and Reconstructive Surgeons; Nov. 1993.

Website: www.greer-medical.com; Greer Medical, Inc., SeromaCath Wound Drainage System (4 pages), 2011.

Axiom Medical, Inc. SeroVac II and SeroVac Series drainage products (2 pages), May 11, 2004.

Greer Medical, Inc., SeromaCath Wound Drainage System pamphlet and instructions for use. (3 pages), 2011.

"Patient-Controlled Transdermal Fentanyl Hydrochloride vs. Intravenous Morphine Pump for Postoperative Pain" article in JAMA, Mar. 17, 2004—vol. 291, No. 11 (9 pages).

* cited by examiner

Fig. 5

INFILTRATION CANNULA

CROSS-REFERENCE TO RELATED APPLICATIONS

The present application is a continuation application of U.S. application Ser. No. 12/004,778, filed on Dec. 21, 2007 now abandoned which is a divisional application of U.S. application Ser. No. 10/877,566, filed on Jun. 25, 2004 now abandoned which is a continuation-in-part application of U.S. patent application Ser. No. 10/442,370, filed on May 21, 2003 now abandoned and is related to application Ser. No. 10/877,337, filed on Jun. 25, 2004, now U.S. Pat. No. 7,572,613, issued on Aug. 11, 2009 and pending application Ser. No. 11/800,355, filed on May 4, 2007, the disclosures of which are expressly incorporated herein by reference.

STATEMENT RE: FEDERALLY SPONSORED RESEARCH/DEVELOPMENT

Not Applicable

BACKGROUND OF THE INVENTION

Definitions

Tumescent Technique:

The tumescent technique is a method of subcutaneous drug delivery of large volumes of very dilute medication together with dilute epinephrine in isotonic solution of crystalloid infiltrated directly into subcutaneous fat or muscle to produce swelling and firmness, or tumescence, of the targeted tissues, and thus produce very slow systemic absorption as a result of intense subcutaneous vasoconstriction.

Tumescent Drug Delivery:

Tumescent drug delivery refers to the tumescent technique for delivering a drug into the subcutaneous space. Drugs other than lidocaine can be administered by means of tumescent delivery, that is, by subcutaneous infiltration of extremely dilute drug, with or without epinephrine as a vasoconstrictor.

Tumescent Local Anesthesia (TLA) is local anesthesia produced by direct infiltration into subcutaneous tissue of large volumes of very dilute lidocaine and epinephrine in a crystaloid solution such as physiologic saline (NaCl) or lactated Ringer's solution.

Tumescent Local Anesthetic Solution (TLA Solution) is the local anesthetic solution used to produce TLA. Typically, a TLA Solution consists of a 10 to 20 fold dilution of commercially available concentration of lidocaine and epinephrine. Thus, a commercial solution of lidocaine and epinephrine contains 10 grams of lidocaine per liter (10 gm/L) and 10 milligrams of epinephrine per liter. In contrast TLA Solution typically contains less than 1 gm/L lidocaine and epinephrine (1 mg/L). Typically the volume of infiltrated TLA Solution is so large that the skin and subcutaneous tissue becomes tumescent, in other words swollen and firm.

The present invention relates in general to cannulas and in particular to an infiltration cannula that allows for intermittent infiltration of fluids, such as a local anesthetic.

Many medical procedures require infiltration of fluids, such as a local anesthetic. One method of infiltration of local anesthetic is via an infiltration cannula. Infiltrators are known as sprinkler-tip or Klein™ (the present applicant) needle infiltrators. These cannulas are constructed out of a rigid stainless steel and have one or more apertures, which are typically round or oval, and are distributed about the distal end of the cannula. The apertures are distributed over about 15% to 25% or less than 5.0 cm. of the distal end of the cannula needle. These traditional infiltration cannulas are intended to be inserted through a small incision in the patient's skin and then moved in and out through the subcutaneous tissue while a dilute solution of local anesthetic (or other pharmaceutical solution) is ejected through the distal apertures. Such infiltrators typically have a blunt tip and require the placement of a small hole (made by a one mm skin-biopsy punch or a small surgical blade) through which the blunt tipped cannula can be passed. The piston-like in and out motion of the cannula causes the patient discomfort.

Another method of fluid insertion is via a peripherally inserted central catheter, also called a PICC line comprising an elongate plastic tube that is placed inside a vein of the patient. PICC lines are typically used for procedures requiring delivery of fluids over a prolonged period of time. For example, a PICC line may be used when a patient needs to receive intravenous (IV) fluids, such as medication or nutrients over a prolonged period of time, such as a week or more.

The On-Q® Pain Management System marketed by I-Flow® Corporation employs a PICC line type system for continuously providing local anesthetic. This system provides prolonged local anesthesia by means of an elastomer (elastic container) device that continuously infiltrates a solution of local anesthesia over many hours. The On-Q® device comprises a long soft flexible tube with many small holes arranged along a significant portion of the tube. The On-Q® device is designed to be initially positioned within a surgical wound at the time of surgery. After the surgical wound is closed, the On-Q® device permits slow steady infiltration of a local anesthetic solution into the wound, thereby attenuating post-operative pain. The On-Q® device cannot be inserted through a tiny hole in the skin into subcutaneous tissue. Thus there is a need for a simple device that can permit the direct percutaneous insertion of a multi-holed infiltration cannula into subcutaneous tissue for the localized delivery of medications such as local anesthetics, chemotherapeutic agents, or crystalloids for parenteral hydration.

Traditional techniques for subcutaneous injection of local anesthetic solutions use a high-concentration/low-volume of local anesthetic. This is associated with a rapid systemic absorption of the local anesthetic. In order to achieve a prolonged local anesthetic effect, the traditional techniques for using local anesthetics necessitate either frequent repeated injections or slow continuous subcutaneous infusion of the local anesthetic. As described above, repeated injections or piston-like movement of the cannula causes patient discomfort. Slow continuous infiltration may not be desirable in certain situations. Furthermore, continuous infiltrations restrict patient movement for extended periods of time which also cause the patient discomfort. Thus, there is a need for a system for infiltration of a local anesthetic into subcutaneous tissue which decreases patient discomfort, and allows prolonged local anesthesia either by rapid bolus injections or continuous slow infiltration. Furthermore there is a need for a devise that can provide pre-emptive local anesthesia before a surgical wound is created. There is also a need for a percutaneously-insertable infiltration cannula, with applications that are unrelated to the delivery of local anesthesia, which can be easily inserted by rescuers with minimal clinical skill or training. One example is the need for a cannula that permits emergency fluid resuscitation in situations where an IV cannot be established such as nighttime military combat conditions where using a flash light to establish an IV access would be extremely dangerous. Another example is the need to provide emergency fluid resuscitation to large numbers of patients in acute epidemic diarrhea (dehydration) associated with biological warfare, or mass-trauma situations such as a natural disaster (earth quake) or terrorist attack. There is also a need for a device that can easily provide localized fluid resuscitation to burn victims whereby fluid is infiltrated into the subcutaneous tissue directly subjacent to burned skin.

BRIEF SUMMARY OF THE INVENTION

The present invention comprises an infiltration cannula and method of using the infiltration cannula during an infiltration procedure. The infiltration cannula preferably includes: a flexible cannula, a hub, and a rigid stylet. The flexible cannula has a proximal end and a distal end. The flexible cannula also has a plurality of apertures disposed in a pattern about the distal end. The apertures are configured to infiltrate fluid into the subcutaneous tissue of a patient. The hub is configured to be held by a person performing the infiltration procedure. The hub has a first end and an opposing second end. The first end is attached to the proximal end of the flexible cannula and the second end includes a connector configured to connect to an input source for receiving the fluid to be infiltrated into the subcutaneous tissue of the patient. The fluid flows from the connector, through the hub and into the flexible cannula.

The flexile cannula may be manufactured of plastic and the rigid stylet may be fabricated from stainless metal or rigid plastic. The distal end of the cannula is closed to cover the tip of the rigid stylet or open with a hole allowing the tip of the rigid stylet to protrude through. The tip of the rigid stylet is either sharp to directly insert through the skin of the patient, or so blunt that a skin incision is required to permit insertion of the rigid stylet and the cannula into the subcutaneous space. The stylet may be formed to have either a solid or hollow cross-sectional configuration.

The apertures may be arranged in a helical pattern or in a spiral pattern.

The apertures may be distributed over about 33% to about 90% of the distal end of the tubular needle.

The apertures may be round or oval. The size of the apertures need not necessarily be equal.

The fluid may comprise a local anesthetic or any other therapeutic solution.

The infiltration procedure may be performed in conjunction with conventional medical procedures such as liposuction, but additionally may simply be used as a mode of systemic drug delivery, or systemic fluid replacement therapy.

A method of infiltrating fluid into subcutaneous tissue of a patient using an infiltration cannula, such as the one described above may include the following steps.

A rigid stylet is inserted through a flexible infiltration cannula. The infiltration cannula is inserted through a patient's skin and into the subcutaneous tissue or muscle tissue of the patient at a desired site with the stylet serving as a guiding wire. After the stylet let is withdrawn from the cannula, a fluid is provided from a fluid source via the connector. The fluid is transported from the connector through the hub and into the flexible cannula. The fluid is ejected from the cannula into the subcutaneous tissue or muscle of the patient via the apertures.

The infiltration cannula used in performing the method preferably includes a connector for receiving the fluid from a fluid source, a hub in communication with the connector and a flexible cannula in communication with the hub. The tubular needle has a plurality of apertures disposed in a pattern about a distal end. The apertures are configured to infiltrate the fluid into the subcutaneous tissue or muscle of the patient.

The above steps may be repeated intermittently, at intervals between a few minutes to many hours.

After the desired amount of fluid has been infiltrated at a given site, the infiltration cannula may be removed or may remain in place for possible additional infiltration.

The infiltration cannula may additionally be inserted at a new site.

Multiple infiltration cannulas (e.g., two) may be used simultaneously. Use of multiple infiltration cannulas prevents disruption of the infiltration process when one infiltration cannula is removed. Multiple infiltrators can be simultaneously inserted into separate areas to facilitate more rapid delivery of fluids.

BRIEF DESCRIPTION OF THE DRAWINGS

These as well as other features of the present invention will become more apparent upon reference to the drawings wherein.

DETAILED DESCRIPTION OF THE INVENTION

As described in further detail below, the present invention takes advantage of the tumescent technique in order to provide intermittent or continuous, brief or prolonged infiltration of local anesthetic, physiologic fluid, antibiotics or other therapeutic solution. The present invention results in a significant decrease in patient discomfort due to the elimination of the piston-like in and out motion of the cannula. Once the cannula is positioned in place, there is no need to repeatedly move the cannula in and out through the tissue in order to deliver the fluid to a wide area. Using the tumescent technique and stainless steel versions of the present invention, the time needed in order to complete the infiltration of a targeted anatomic area is reduced to nearly half of the time required when using traditional prior art cannulas. The device and method of the present invention can use multiple (e.g., two or more) infiltration cannulas simultaneously. While one cannula is actively dispersing tumescent fluid into the subcutaneous tissue, the surgeon can reposition a second infiltration cannula. This allows the infiltration process to proceed without interruption, whereas prior art techniques of infiltration must be ceased each time the cannula is withdrawn from the skin and re-inserted into another direction.

The flexible cannula version of the present invention provides a means for relatively rapid fluid resuscitation in emergency situations such as when establishing an intravenous (IV) access is not feasible. The flexible cannula may have important applications as in treating a wounded soldier in night-time combat conditions when establishing an IV access in total darkness is nearly impossible or using a flash light might attract enemy fire. The flexible cannula may similarly have important applications in other areas of use such as treating mass-casualty victims suffering hypovolemia as a result of epidemic infections, biologic warfare, or trauma such as explosions, burns or radiation exposure. The flexible cannula similarly has applications in surgical patients wherein the surgeon can provide localized pre-operative pre-emptive analgesia and simultaneously provide tumescent delivery of a prophylactic dose of an antibiotic aimed precisely at tissues targeted for surgical intervention.

As is well known, the tumescent technique was discovered by Jeffrey Alan Klein, M.D. (the present applicant) in 1985. Dr. Klein first published a description of the tumescent technique in 1987 when he described the use of dilute lidocaine and epinephrine to permit liposuction totally by local anesthesia. The technique for tumescent local anesthesia is well known in dermatologic and plastic surgery literature. A detailed description of the tumescent technique has not been published in anesthesiology literature, and therefore, the unique benefits of the tumescent technique are not well recognized by anesthesiologists.

The tumescent technique comprises a drug delivery system that takes advantage of a recently discovered reservoir effect of injecting a relatively large volume of relatively dilute solution of a drug into the subcutaneous tissue.

The present invention takes advantage of the tumescent reservoir phenomenon for one of its important applications. After a large volume of fluid containing dilute epinephrine is injected into subcutaneous tissue, the epinephrine-induced vasoconstriction dramatically slows the systemic absorption of the fluid. In effect, this large volume of subcutaneous fluid behaves in a fashion that is analogous to the behavior of a slow-release tablet in the stomach after oral ingestion. Although there is a relatively large total amount of drug in the patients body, the drug is isolated from the systemic circulation by the fact that only the drug on the outer boundary of the mass of drug is the available for absorption, whereas the portion of the drug located within the central portion of the mass of fluid is virtually isolated from the systemic circulation by virtue of profound capillary vasoconstriction. In contrast, when the tumescent fluid does not contain epinephrine there is no clinically significant vasoconstriction after tumescent infiltration, and the tumescent fluid is absorbed relatively rapidly. This has important clinical applications in situations where patients are hypovolemic or dehydrated and unable to be given fluids by mouth or intravenously. The tumescent technique permits rapid systemic hydration by direct subcutaneous or intramuscular injection of a large volume of fluid through a multi-fenestrated infiltration cannula described in this invention.

There is a prior art technique known as hypodermoclysis wherein a fluid is slowly and continuously infiltrated subcutaneously using a type of steel hypodermic needle, known as a butterfly needle, having a single distal aperture in order to provide fluid to patients who cannot be given fluids by mouth and for whom an IV access cannot be established. Typically hypodermoclysis is used in the treatment of infants, or cancer patients, in which IV access is not easily achieved. The technique of hypodermoclysis is typically used to deliver relatively small volumes of fluid, for example an adult might receive 70 ml per hour. At this small hourly volume hypodermoclysis is not an efficient method for the rapid systemic delivery of fluid in emergency situations that might require two to four liters per hour. The reason is that when using a cannula with only a single distal aperture, the local interstitial fluid pressure increases rapidly immediately adjacent to the single aperture as fluid infiltrates locally, which in turn dramatically slows the rate of subsequent fluid flow into the area. In contrast, the multiple apertures formed along the length of the cannula as described in the present invention, distribute the fluid throughout a much larger volume tissue before there can be a sufficient increase in the interstitial fluid to decrease the rate of additional infiltration. Further more, it is common practice to infiltrate the tumescent fluid into the subcutaneous space under augmented external pressure provided by an external peristaltic pump specifically designed for tumescent infiltration. By way of example and not limitation, a preferred suitable peristaltic infiltration pump is described in pending U.S. patent application Ser. No. 10/811,733, filed Mar. 29, 2004, entitled INFILTRATION PUMP HAVING INSULATED ROLLERS AND PROGRAMMABLE FOOT PEDAL, the disclosure of which is expressly incorporated herein by reference.

The peristaltic pump provides a sufficient degree of pressure to easily overcome the localized increased interstitial pressure associated with the local effects of a tumescent infiltration. On the other hand, in situations where a peristaltic infiltration pump is not available, such as in remote locations without any available electrical power, the present invention still permits relatively rapid tumescent infiltration by virtue of the multiple holes distributed along the length of the flexible cannula. Furthermore, external hydrostatic pressure can be applied to the fluid flowing into the flexible cannula from the fluid reservoir by means of gravitational force derived from elevating the reservoir one to two meters above the patient. When using gravity to augment the flow of tumescent fluid, the infiltration process can be continuous or intermittent. In exemplary embodiments, the intermittent injections are administered at intervals ranging from every few minutes to eight to twelve hours or more.

With the tumescent technique for local anesthesia, a large volume of dilute solution of local anesthesia and epinephrine is injected into the subcutaneous space resulting in a large bolus (or reservoir) of solution. The profound vasoconstrictive effect (shrinking of the capillaries) caused by the dilute epinephrine, produces a dramatic delay in the systemic absorption of the local anesthetic, which prolongs the anesthetic effects of tumescent anesthesia for eight to sixteen times longer than traditional techniques.

Figure 1:
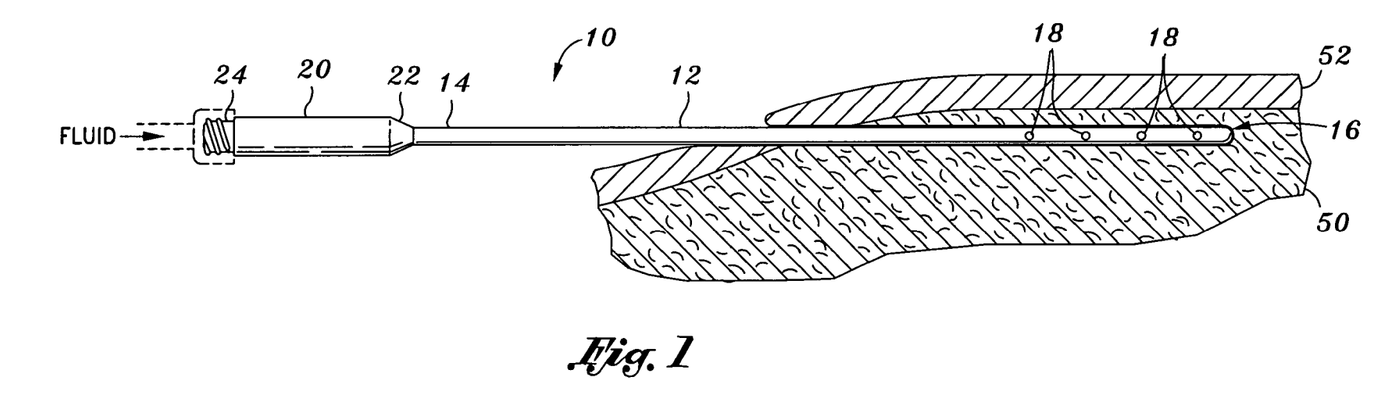
FIG. 1 is a side elevation view of a stainless steel infiltration cannula with a closed tip shown inserted in subcutaneous tissue shown in partial cross section.
Figure 2:
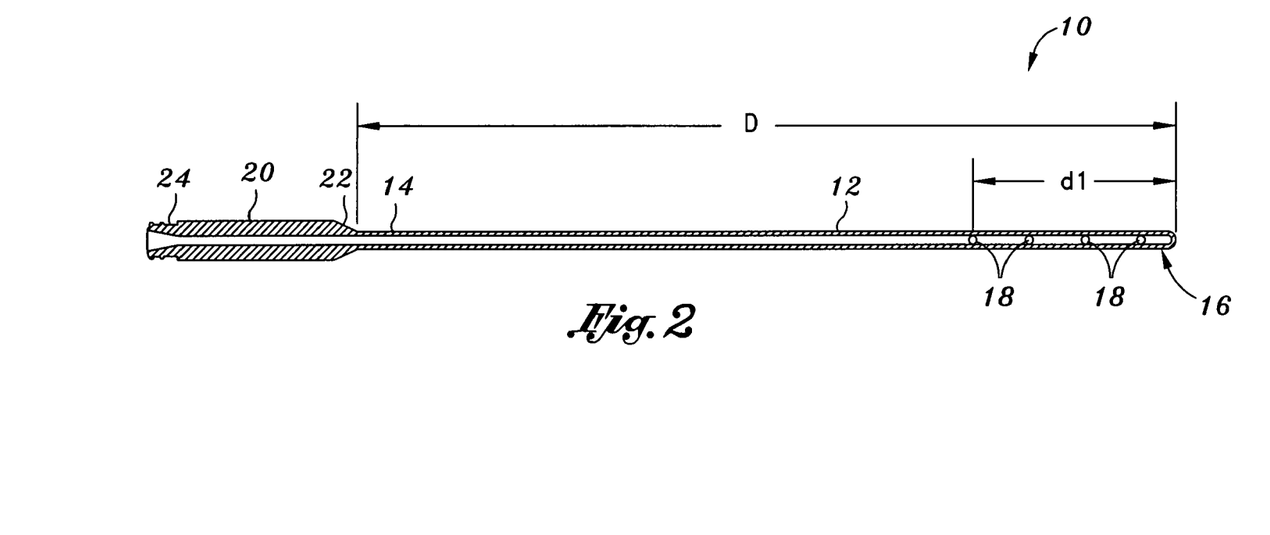
FIG. 2 is a section view of the infiltration cannula shown in FIG. 1.

Referring now to the drawings wherein the showings are for purposes of illustrating preferred embodiments of the present invention only, and not for purposes of limiting the same, FIGS. 1 and 2 illustrate a stainless steel (reusable) infiltration cannula 10 and FIGS. 3-4 and 6-7 illustrate a (single use) plastic infiltration cannula 30. The cannula 10, 30 can be inserted under the skin 52 and into the subcutaneous tissue 50 and tumescent local anesthesia can be infiltrated once every eight to twelve hours.

Stainless steel infiltration cannulas 10, such as the one shown in FIGS. 1 and 2, are formed having precision high quality and are preferably reusable. These cannulas can be used to provide tumescent local anesthesia for surgical procedures, such as liposuction, which require tumescent local anesthesia over a relatively large area.

The cannula 10 includes a tubular needle portion 12 which has a proximal end 14 and a distal end 16. The proximal end 14 of the tubular needle 12 is attached to a hub 20 that is used by the anesthesiologist or surgeon to grasp and hold the cannula 10 during the infiltration procedure. The hub 20 is connected to the tubular needle 12 at a first end 22 and has a connector 24, such as a luer lock, at an opposing second end.

The connector 24 is connected to a fluid source, such as tubing connected to an IV bag. Fluid enters the cannula 10 via the connector 24.

In exemplary embodiments, the tip at the distal end 16 is closed. The local anesthetic is infiltrated into the patient via apertures 18 located proximate the distal end 16 of the tubular needle 12 of the cannula 10. In exemplary embodiments, the apertures 18 are disposed along the distal end 16 of the cannula 10 in a spiral or helical pattern and are distributed over the distal 33% to 90% of the tubular needle 12 of the cannula 10. For example, if the length of the tubular needle D is 15 cm and the apertures 18 at the distal end 16 cover a length d1 of 5 cm, the pattern of apertures of the cannula 10 are preferably distributed over 33% of the tubular needle 12 of the cannula 10.

The proximal portion 14 of the cannula 10 is preferably devoid of apertures in order to prevent fluid from leaking out of the cannula insertion site in the skin.

Flexible plastic infiltration cannulas 30, such as the one shown in FIGS. 3, 4, 6 and 7 are single use cannulas and can be used in one of several unique ways. First, an anesthesiologist or surgeon can insert an infiltration cannula 30 with stylet 46 into the subcutaneous tissue 50, remove the stylet 46, then attach an IV tubing to the infiltrator and inject tumescent local anesthesia into the targeted area without subsequent repositioning of the infiltration cannula 30. The plastic flexible nature of the infiltration cannula 32 of the disposable plastic cannula 30 allows the patient to move or change position of the body without risk of injury that might result if a patient moves while a rigid steel cannula is inserted.

Figure 6:
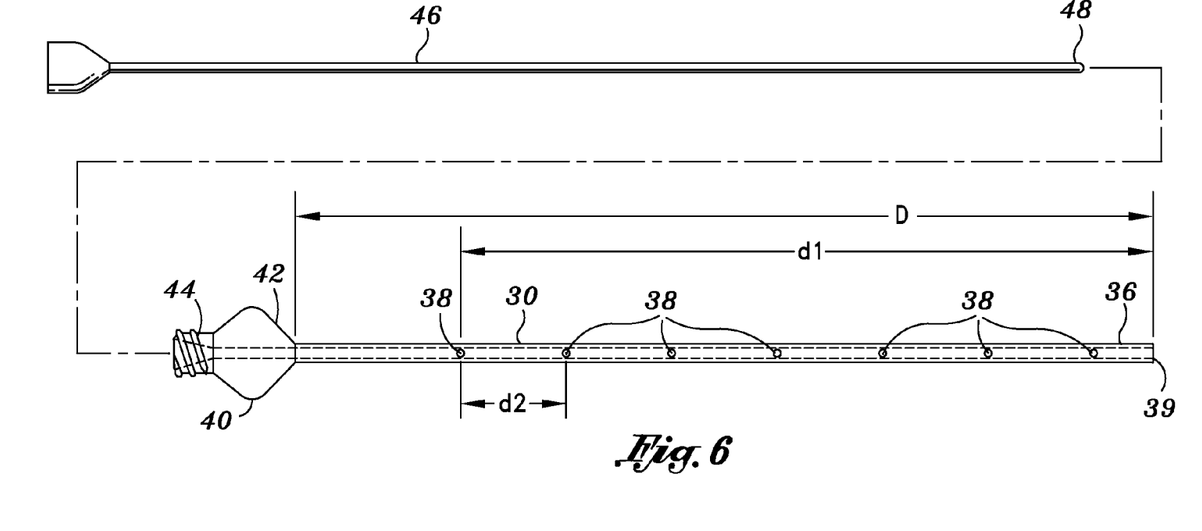
FIG. 6 is an exploded side elevation view of a plastic infiltration cannula through which a blunt-tipped stylet can be inserted.
Figure 6A:
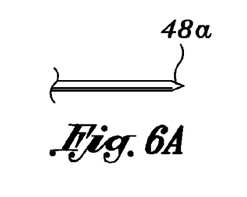
FIG. 6A illustrates a sharp-tipped stylet insertable into the cannula shown in FIG. 6.
Figure 7:
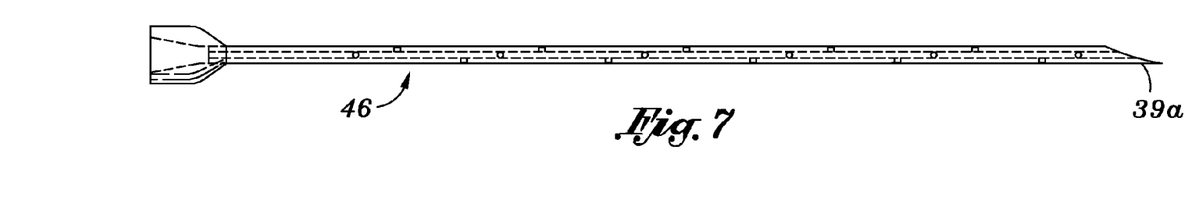
FIG. 7 is a side view of a sharp-tipped stylet insertable through the plastic infiltration cannula of FIG. 6.

Preferably, the stylet 46 is formed of metal, e.g., stainless steel, or of a rigid plastic material. The plastic cannula 30 can be blunt-tipped with the metal stylet tip 48 covered by the rounded tip 39 of the plastic cannula 30. Alternatively, the plastic cannula 30 can be open-ended with the stylet 46 extending a short distance past the end 39 of the plastic cannula 30 as shown in FIG. 6. In the case of the open ended cannula, the stylet 46 can be either blunt-tipped (see FIG. 6; requiring a skin incision to permit insertion into the subcutaneous space), or sharp-tipped 48a (see FIG. 6A; permitting the cannula to be inserted directly through the skin and into the subcutaneous space or muscle without requiring a preparatory skin incision). The stylet with sharp tip 48a, 39a can be formed in either a solid or hollow cross-sectional configuration, as shown in FIGS. 6A and 7.

Figure 3:
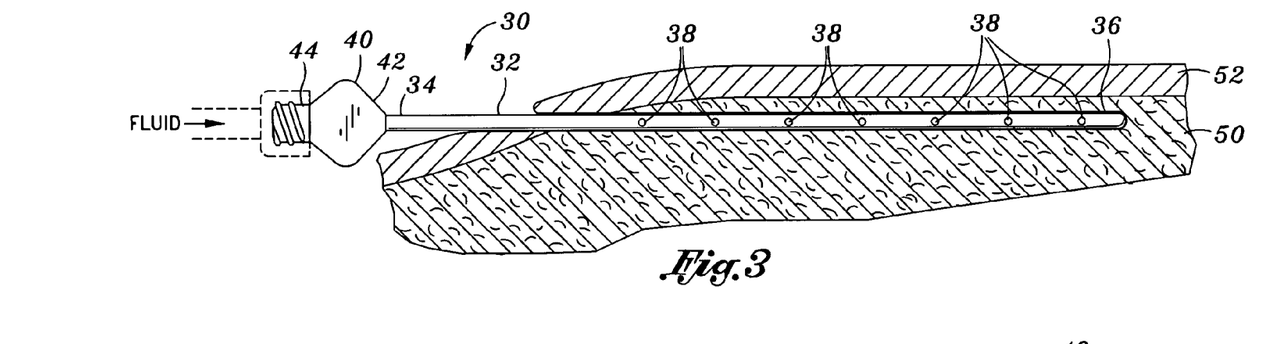
FIG. 3 is a side elevation view of a plastic infiltration cannula with a closed tip shown inserted in subcutaneous tissue shown in partial cross section.
Figure 4:
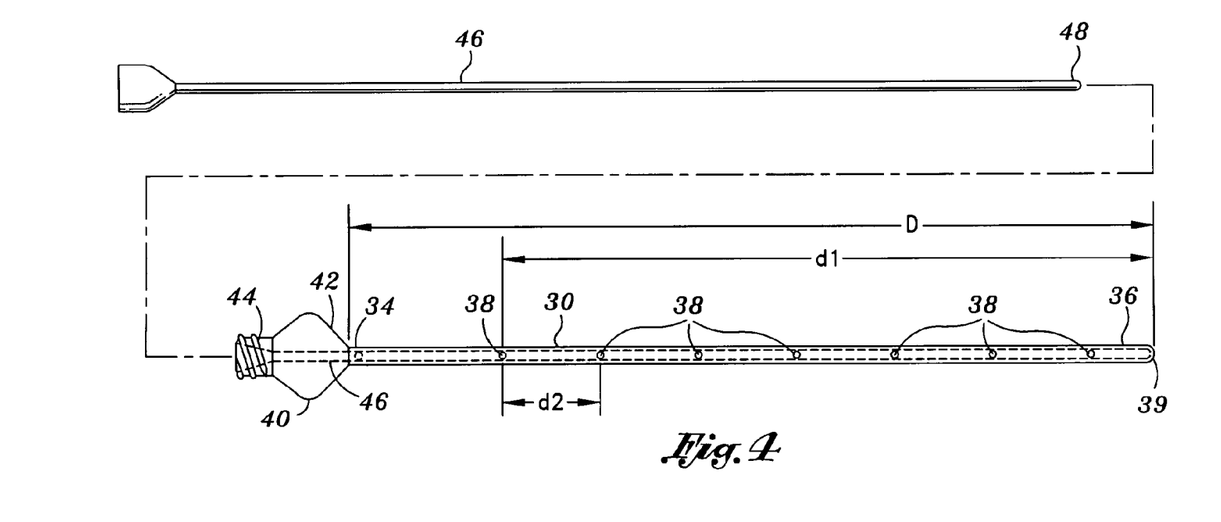
FIG. 4 is an exploded view of the infiltration cannula shown in FIG. 3.

The plastic cannula shown in FIGS. 3 and 4 is similar to an IV catheter except the sharp hollow stylet used for the insertion of an IV catheter can be replaced by a solid obturator/stylet 46 that can be either sharp or blunt tipped. Except for the removable stylet 46, the plastic cannula 30 is similar to the stainless steel cannula 10 shown in FIGS. 1 and 2 and described above. The plastic cannula 30 includes a flexible tubular needle 32 having a proximal end 34 and a distal end 36. The distal end has apertures 38 and the proximal end 34 is devoid of apertures. As stated above, in exemplary embodiments, the pattern of apertures 38 in the cannula 30 are distributed over the distal 33% to 90% of the tubular needle 32 of the cannula 30. For example, if the tubular needle 32 of cannula 30 shown in FIGS. 3 and 4 has a length D of 15 cm and the pattern of apertures are distributed over a length d1 of 13.5 cm, then the apertures 38 are distributed over 90% of the cannula.

A typical infiltration cannula 10, 30 may have a diameter equivalent to 20, 18, 16 or 14 gauge with small apertures 18, 38 placed every 5 mm along the cannula in a spiral or helical pattern. It will be appreciated that the dimensions used herein are exemplary and that the cannula dimensions, range of gauge, length of cannula, relative size shape and pattern of apertures can vary greatly depending upon clinical preference.

The proximal end 34 of the tubular needle 32 shown in FIGS. 3 and 4 is attached to a hub 40 that is used by the anesthesiologist or surgeon to hold the cannula 30 during the infiltration procedure. The hub 40 is connected to the tubular needle 32 at a first end 42 and has a connector 44 at an opposing second end. The connector 44 is connected to a fluid source. As described above and shown in FIG. 4, the stylet 46 can be inserted and removed from the cannula 30.

Infiltration using a plastic infiltration cannula 30, such as the one shown in FIGS. 3 and 4, can be accomplished using an infiltration pump. Alternatively, the force of gravity could be used to push the tumescent fluid into the tissues by hanging a reservoir plastic bag of tumescent local anesthesia (or other dilute drug, such as a chemotherapeutic agent or antibiotics) on an IV pole and connecting bag to the infiltration cannula by an IV line.

Another application is the injection of tumescent local anesthesia into a localized area through which a surgeon plans to make a surgical incision. The effects of vasoconstriction, resulting from the epinephrine in the tumescent local anesthetic solution, within the tumesced tissue minimizes surgical bleeding. In a uniquely preemptive fashion, the present invention can produce, via the pre-operative infiltration of tumescent local anesthesia, prolonged post operative analgesia and also preemptively reduce the risk of surgical wound infections resulting from the bacteriacidal effects of lidocaine.

Yet another application is to provide an easily accessible route for systemic administration of crystalloid fluids/electrolytes for systemic hydration or for other types of drug therapy. Potential clinical applications include emergency resuscitation with systemic fluids in situations where insertion of an IV catheter into a vein cannot be readily achieved. Examples of situations where emergency access for intravenous delivery of fluids might not be possible include acute trauma or burn wound in civilian or military situations. Another application may be the emergency treatment of dehydration associated with prolonged vomiting or diarrhea as a result of chemical warfare or biological warfare (e.g., epidemic cholera among pediatric patients in rural third world settings). A subcutaneous infiltration catheter can easily be introduced by a layman, whereas inserting an IV catheter into a vein of a patient that is severely dehydrated can be difficult even for a skilled physician. Delivery of systemic fluids by subcutaneous infiltration is safer in a zero gravity situation (for example, the Space Station). The addition of a small amount of capillary vasodilator (e.g., methylnicotinamide) to the subcutaneous fluid can be used to accelerate the systemic absorption of the fluid or drug into the intravascular space. Further applicational uses for the present invention are described in co-pending application serial number unknown, filed concurrently herewith entitled DRUG DELIVERY SYSTEM FOR ACCELERATED SUBCUTANEOUS ABSORPTION, the disclosure of which is expressly incorporated herein by reference.

The cannula 10, 30 is intended to be inserted far enough through the skin 52 so that all of the apertures 18, 38 are within the fat 50 or muscle of the patient. Once the cannula 10, 30 is properly positioned, it can remain stationary while the local anesthetic (or other pharmaceutical) solution is injected.

After one portion of the targeted area has been tumesced, the infiltration is briefly terminated (either by turning off the pump or by clamping the IV tubing) while the cannula 10, 30 is repositioned into another area of the subcutaneous tissue. The infiltration is then restarted with the cannula stationary in its new position.

The infiltrator 10, 30 can also be used in the traditional mode whereby the cannula 10, 30 is moved through the targeted tissue while the fluid is simultaneously pumped through the cannula 10, 30 and into the subcutaneous tissue 50.

Another unique aspect of the tumescent technique's reservoir effect is that one can conveniently achieve a long, slow, steady absorption of a drug delivered to the subcutaneous space 50 using periodic injections of a tumescent solution. In certain situations, using a slow IV infusion, the alternative technique, can achieve a slow systemic absorption of a drug but may be difficult, require greater clinical expertise, be more expensive, and therefore, less practical than the technique described herein.

Figure 5:
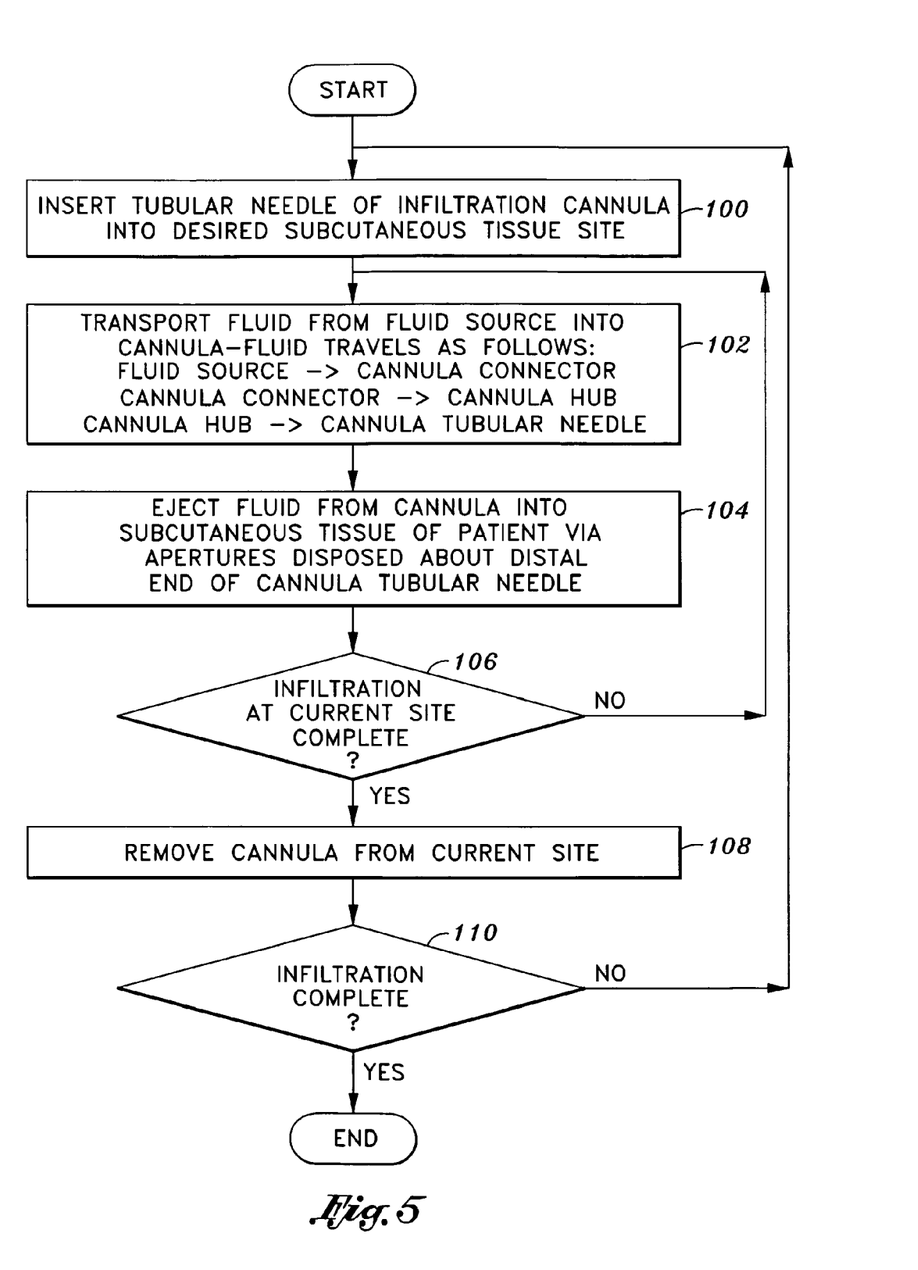
FIG. 5 is a flow diagram illustrating an exemplary procedure for using an infiltration cannula such as the one shown in FIG. 1 or the one shown in FIG. 3.

FIG. 5 is a flow diagram illustrating steps performed in an exemplary infiltration procedure using a cannula 10, 30 such as the one shown in FIGS. 1 and 2 or the one shown in FIGS. 3 and 4, respectively. The procedure begins by inserting the tubular needle 12, 32 of the infiltration cannula 10, 30 into a desired subcutaneous tissue site 50, e.g., via an incision in the patient's skin 52 (block 100). Fluid is then transported from the fluid source (e.g., an IV bag) into the cannula 10, 30 via the connector 24, 44 that is connected to the fluid source. The fluid is transported from the connector 24, 44 through the hub 20, 40 and into the tubular needle 12, 32 (block 102). The fluid is then ejected from the cannula 10, 30 into the subcutaneous tissue 50 of the patient via the apertures 18, 38 at the distal end 16, 36 of the tubular needle 12, 34 of the cannula 10, 30 (block 104).

The fluid is transported (block 102) and ejected (block 104) until infiltration at the current site is completed (yes in decision block 106). The fluid can be injected into multiple sites in order to distribute the solution over a greater area.

Infiltration at a particular site may be deemed complete upon emptying of the fluid source or based on the anesthesiologist or surgeon's decision to stop the infiltration at the current site. After one portion of the targeted area has been tumesced, the infiltration can be briefly terminated (either by turning off the pump or by clamping the IV tubing) while the cannula 10, 30 is repositioned into another area of the subcutaneous tissue. The infiltration may then be restarted with the cannula stationary in its new position. If the infiltration at a site is complete (yes in decision block 106), the cannula is removed from the current site (block 108). If the infiltration at the current site is not complete (no in decision block 106), fluid is transported from the fluid source (block 102) and ejected into the subcutaneous tissue (block 104) until infiltration at the site is complete (yes in decision block 106).

If infiltration is complete at the current site (yes in decision block 106) but infiltration is not complete (no in decision block 110), the tubular needle 12, 32 of the infiltration cannula 10, 30 is inserted into a new area of subcutaneous tissue 50. The process described above is performed until the infiltration process is complete (yes in decision block 110). This process can be continuous or repeated intermittently.

As described above, multiple infiltration cannulas (e.g., can be used at once). Thus, a second or additional cannulas can be inserted (block 100) at the same time as a first cannula is being removed (block 108). Thus, the infiltration process need not be interrupted in order to reposition a single cannula.

Additional modifications and improvements of the present invention may also be apparent to those of ordinary skill in the art. Thus, the particular combination of parts described and illustrated herein is intended to represent only a certain embodiment of the present invention, and is not intended to serve as a limitation of alternative devices within the spirit and scope of the invention.

What is claimed is:

1. An infiltration cannula for delivering a multi liter amount of fluid during an infiltration procedure, the infiltration cannula comprising:
    a rigid stylet;
    a flexible tubular cannula having a length of about 15 cm with the rigid stylet disposed within the flexible tubular cannula, the flexible tubular cannula comprising:
        a proximal portion;
        a distal portion defining a distal end, the distal end being open with a hole, and a tip of the rigid stylet protruding through the hole; and
        a plurality of apertures disposed in a pattern about the distal portion so that the plurality of apertures cover a distal 90% of the cannula, the apertures configured to infiltrate the multi-liter amount of fluid into subcutaneous tissue or muscle of a patient;
    a hub configured to be held by a person performing the infiltration procedure, the hub having a first end and an opposing second end, the first end being attached to the proximal portion of the flexible tubular cannula, the second end comprising a connector for receiving the fluid to be infiltrated into the subcutaneous tissue of the patient, the fluid flowing from the connector, through the hub and into the flexible tubular cannula; and
    a container connectable to the connector of the hub and operative to continuously deliver the multi-liter amount of the fluid through the hub and the flexible tubular cannula.

2. The infiltration cannula as recited in claim 1, wherein the tip of the rigid stylet is sharp to directly insert through the skin of the patient without a prepatory skin incision.

3. The infiltration cannula as recited in claim 1, wherein the rigid stylet is blunt tipped to require a prepatory skin incision to permit insertion of the stylet and flexible tubular cannula through the skin of the patient.

4. An infiltration cannula for use in an infiltration procedure, the infiltration cannula comprising:
    a tubular needle being about 15 cm long and having a plurality of apertures disposed in a pattern and distributed over a distal 70% to 90% of the tubular needle, the apertures being configured to infiltrate fluid into subcutaneous tissue of a patient, a proximal portion of the tubular needle being devoid of apertures to prevent leakage of the fluid from the needle to outside of a patient;
    a hub configured to be held by a person performing the infiltration procedure, the hub having a first end and an opposing second end, the first end being attached to the proximal end of the tubular needle, the second end connectable to a container for continuous delivery of a multi liter amount of fluid through the hub and the tubular needle.

5. The cannula of claim 4 wherein the plurality of apertures is disposed about the distal 80% to 90% portion of the needle.

6. The cannula of claim 4 wherein the plurality of apertures is disposed about the distal 90% portion of the needle.

7. An infiltration cannula for use in an infiltration procedure, the infiltration cannula comprising:
    a tubular needle having a length of about 15 cm, the needle having a plurality of apertures disposed in a pattern and distributed only over a distal 13.5 cm of the tubular needle, the apertures being configured to infiltrate fluid into subcutaneous tissue of a patient, a proximal portion of the tubular needle being devoid of apertures to prevent leakage of the fluid from the needle to outside of a patient;

a hub configured to be held by a person performing the infiltration procedure, the hub having a first end and an opposing second end, the first end being attached to the proximal end of the tubular needle, the second end connectable to a container for continuous delivery of a multi liter amount of fluid through the hub and the tubular needle.

8. The cannula of claim 7 wherein the needle is rigid.

9. The cannula of claim 7 wherein a distal end of the needle is closed.

10. The cannula of claim 7 further comprising a stylet insertable into a lumen of the needle.

11. An infiltration cannula for delivering a multi liter amount of fluid during an infiltration procedure, the infiltration cannula comprising:

a rigid stylet:

a flexible tubular cannula having a length of about 15 cm with the rigid stylet disposed within the flexible tubular cannula, the flexible tubular cannula comprising:

a proximal portion;

a distal portion defining a distal end, the distal end being open with a hole, and a tip of the rigid stylet protruding through the hole; and a plurality of apertures disposed in a pattern about the distal portion so that the plurality of apertures cover a distal 50% to 90% of the cannula, the apertures configured to infiltrate the multi-liter amount of fluid into subcutaneous tissue or muscle of a patient;

a hub configured to be held by a person performing the infiltration procedure, the hub having a first end and an opposing second end, the first end being attached to the proximal portion of the flexible tubular cannula, the second end comprising a connector for receiving the fluid to be infiltrated into the subcutaneous tissue of the patient, the fluid flowing from the connector, through the hub and into the flexible tubular cannula.

12. The cannula of claim 11 wherein the plurality of apertures is disposed about 60% to 90% of the cannula.

13. The cannula of claim 11 wherein the plurality of apertures is disposed about 70% to 90% of the cannula.

14. The cannula of claim 11 wherein the plurality of apertures is disposed about 80% to 90% of the cannula.

15. The cannula of claim 11 wherein the plurality of apertures is disposed about 90% of the cannula.

* * * * *